US012382265B2

(12) United States Patent
McClellan

(10) Patent No.: US 12,382,265 B2
(45) Date of Patent: Aug. 5, 2025

(54) SYSTEMS AND METHODS FOR AUTOMATIC PAIRING OF DEVICES

(71) Applicant: Indie Health LLC, Del Mar, CA (US)

(72) Inventor: Clint McClellan, Del Mar, CA (US)

(73) Assignee: Indie Health LLC, Del Mar, CA (US)

( * ) Notice: Subject to any disclaimer, the term of this patent is extended or adjusted under 35 U.S.C. 154(b) by 0 days.

(21) Appl. No.: 18/374,518

(22) Filed: Sep. 28, 2023

(65) Prior Publication Data

US 2024/0179503 A1     May 30, 2024

Related U.S. Application Data

(63) Continuation of application No. 17/887,738, filed on Aug. 15, 2022, now Pat. No. 11,785,438, which is a (Continued)

(51) Int. Cl.

| H04B 7/00 | (2006.01) |
|---|---|
| A61B 5/00 | (2006.01) |
| A61B 5/022 | (2006.01) |
| G16H 10/60 | (2018.01) |
| G16H 40/67 | (2018.01) |
| H04M 1/72412 | (2021.01) |
| H04W 4/80 | (2018.01) |
| H04W 8/26 | (2009.01) |

(Continued)

(52) U.S. Cl.
CPC ............... *H04W 4/80* (2018.02); *A61B 5/002* (2013.01); *A61B 5/0022* (2013.01); *A61B 5/022* (2013.01); *G16H 10/60* (2018.01); *G16H 40/67* (2018.01); *H04M 1/72412* (2021.01); *H04W 8/26* (2013.01); *H04W 12/06* (2013.01); *G06F 16/24* (2019.01); *H04L 2101/622* (2022.05)

(58) Field of Classification Search
CPC ................................. H04W 4/80; G16H 40/63
USPC ......................................................... 455/41.2
See application file for complete search history.

(56) References Cited

U.S. PATENT DOCUMENTS

| 9,774,497 B2 * | 9/2017 | Britt ....................... H04L 12/283 |
| 10,701,746 B2 * | 6/2020 | McClellan ............. G16H 40/20 |

(Continued)

FOREIGN PATENT DOCUMENTS

| CN | 102541567 A | 7/2012 |
| CN | 103546987 A | 1/2014 |

(Continued)

*Primary Examiner* — Marceau Milord
(74) *Attorney, Agent, or Firm* — Procopio, Cory Hargreaves & Savitch LLP

(57) ABSTRACT

A system comprising a user device having a user identifier (ID), short range communication interface, an application, and a software development kit (SDK) layer; a remote system communicatively coupled to the user device and the application, and configured to obtain the user ID, obtain a plurality of device IDs associated with a plurality of remote devices, associate the user ID with the plurality of device IDs, and provide the plurality of device IDs to the application based on the user ID; wherein the application is configured to receive the plurality of device IDs from the remote system, cause the user device to automatically pair with the plurality of remote devices based on receiving the plurality of device IDs, and receive data from a remote device of the plurality of remote device via the short range communication interface of the user device.

11 Claims, 4 Drawing Sheets

Related U.S. Application Data continuation of application No. 16/915,810, filed on Jun. 29, 2020, now Pat. No. 11,419,168, and a continuation of application No. 16/915,813, filed on Jun. 29, 2020, now Pat. No. 11,418,939, said application No. 16/915,810 is a continuation of application No. 15/793,903, filed on Oct. 25, 2017, now Pat. No. 10,701,746, said application No. 16/915,813 is a continuation-in-part of application No. 15/793,903, filed on Oct. 25, 2017, now Pat. No. 10,701,746.

(51) Int. Cl.
*H04W 12/06* (2021.01)
*G06F 16/24* (2019.01)
*H04L 101/622* (2022.01)

(56) References Cited

U.S. PATENT DOCUMENTS

| | | | |
|---|---|---|---|
| 11,061,798 B1 | 7/2021 | Jain et al. | |
| 11,080,701 B2* | 8/2021 | Scott | G06Q 20/40 |
| 11,418,939 B2* | 8/2022 | McClellan | H04W 12/50 |
| 11,419,168 B2* | 8/2022 | McClellan | H04W 76/11 |
| 11,785,438 B2* | 10/2023 | McClellan | A61B 5/002 |
| | | | 370/328 |
| 2008/0058900 A1 | 3/2008 | Berthelsdorf et al. | |
| 2009/0292178 A1 | 11/2009 | Ellis et al. | |
| 2010/0205209 A1 | 8/2010 | Jokinen | |
| 2011/0282931 A1 | 11/2011 | Chen et al. | |
| 2012/0182939 A1* | 7/2012 | Rajan | A61B 5/002 |
| | | | 370/328 |
| 2015/0220696 A1 | 8/2015 | Lekutai et al. | |
| 2016/0072677 A1 | 3/2016 | Gupta et al. | |
| 2016/0080892 A1 | 3/2016 | Basalamah et al. | |
| 2016/0197772 A1* | 7/2016 | Britt | G08C 17/02 |
| | | | 370/254 |
| 2016/0328576 A1 | 11/2016 | Howley | |
| 2017/0017958 A1* | 1/2017 | Scott | G06Q 20/40 |
| 2017/0061272 A1 | 3/2017 | Deliwala et al. | |
| 2018/0049257 A1 | 2/2018 | Liu et al. | |
| 2018/0116560 A1 | 5/2018 | Quinn et al. | |
| 2021/0152366 A1* | 5/2021 | Wang | G06F 21/645 |

FOREIGN PATENT DOCUMENTS

| | | |
|---|---|---|
| CN | 105357629 A | 2/2016 |
| CN | 106413124 A | 2/2017 |
| EP | 2849473 A1 | 3/2015 |
| EP | 2849473 B1 | 4/2018 |
| WO | 2015047681 A1 | 4/2015 |
| WO | 2017109663 A1 | 6/2017 |

* cited by examiner

SYSTEMS AND METHODS FOR AUTOMATIC PAIRING OF DEVICES

CROSS REFERENCE TO RELATED APPLICATIONS

This application is a Continuation of U.S. patent application Ser. No. 17/887,738, filed Aug. 15, 2022, which is a Continuation of U.S. patent application Ser. No. 16/915,813, filed on Jun. 29, 2020, now U.S. Pat. No. 11,418,939, issued Aug. 16, 2022, which is a continuation in part of U.S. patent application Ser. No. 15/793,903, filed on Oct. 25, 2017, now U.S. Pat. No. 10,701,746, issued on Jun. 30, 2020. This application is also a Continuation of U.S. patent application Ser. No. 16/915,810, filed on Jun. 29, 2020, now U.S. Pat. No. 11,419,168, issued Aug. 16, 2022, which is a continuation of U.S. patent application Ser. No. 15/793,903, filed Oct. 25, 2017, now U.S. Pat. No. 10,701,746, issued on Jun. 30, 2020. All of the contents of which are incorporated herein by reference in their entirety.

BACKGROUND

1. Technical Field

The embodiments described herein are related to remote devices and more particularly to automatically pairing such device with a mobile device and an application running thereon.

2. Related Art mHealth (also written as m-health) and also referred to as connected health is an abbreviation for mobile health, a term used for the practice of medicine and public health supported by mobile devices. The term is most commonly used in reference to using mobile communication devices, such as mobile phones, tablet computers and PDAs, and wearable devices such as smart watches, for health services, information, and data collection. The mHealth field has emerged as a sub-segment of eHealth and Digital Health, the use of information and communication technology (ICT), such as computers, mobile phones, communications satellite, patient monitors, etc., for health services and information. mHealth applications include the use of mobile devices in collecting community and clinical health data, delivery of healthcare information to practitioners, researchers, and patients, real-time monitoring of patient vital signs, and direct provision of care (via mobile telemedicine).

Within the mHealth space, projects operate with a variety of objectives, including increased access to healthcare and health-related information (particularly for hard-to-reach populations); improved ability to diagnose and track diseases; timelier, more actionable public health information; and expanded access to ongoing medical education and training for health workers. According to an analyst firm, around 2.8 million patients worldwide were using a home monitoring service based on equipment with integrated connectivity at the end of 2012. The figure does not include patients that use monitoring devices connected to a PC or mobile phone. It only includes systems that rely on monitors with integrated connectivity or systems that use monitoring hubs with integrated cellular or fixed-line modems; however, a growing segment of mhealth involves interfacing a remote monitoring device, such as a scale, blood pressure cuff glucose meter, activity tracker and any device with short-range wireless connectivity with a PC, laptop, or mobile device, such as a smartphone or tablet.

Today, more than seven million patients now benefit from remote monitoring and the use of connected medical devices as an integral part of their care routines, says a new estimate from Berg Insights. Remote monitoring use grew by 44 percent in 2016 as providers and patients rapidly embraced the convenience of mHealth tools. The use of remote monitoring is expected to continue its growth at a compound annual growth rate (CAGR) of 47.9 percent to reach 50.2 million by 2021.

The ability to use, e.g., a smartphone to interface with remote monitoring devices can potentially, significantly increase the adoption of such devices and can be a catalyst to growing the mhealth space at even greater rates. Currently, as noted above many devices do not interface with a mobile device or PC. Rather, conventional devices more typically interface with a hub that then interfaces with a remote back end system, or the devices themselves include cellular capability that allows them to interface with a back end. The integrators of these systems have complete control of the hub and devices and can readily identify all of the devices and pair them.

The problem with such conventional systems is that the integrators need full control of all of the devices and utilizing a hub incurs additional monthly cellular fees. Many use cases cannot support the additional cost that monthly cellular fees that for a hub to connect the devices.

Interfacing remote monitoring devices with a smartphone can allow patients/consumers to use their own cellular phones and eliminates the cost for a hub or extra cellular line. A problem with conventional devices, however, is that they can be difficult to set up and pair with the mobile device. Often, each device is form a different manufacturer and requires registering the device with a different manufacturer, then trying to pair the device, which can have its own specific pairing protocol or procedure. If a user has multiple devices, then this problem is multiplied. As a result, adoption and interest in the use of and adherence to usage protocols for such devices is limited.

SUMMARY

Systems and methods for automatically pairing multiple remote monitoring devices with a mobile device are described herein.

According to one aspect, a system comprises a mobile device having a user identifier (ID), short range communication interface, an application, and an SDK layer; a device manager server communicatively coupled to the mobile device and the application, and configured to receive the user ID, receive a plurality of device IDs, associate the user ID with the plurality of device IDs in a database, authenticate the application, receive a request from the application, once the application is authenticated, for the plurality of device IDs, and provide the plurality of device IDs to the application based on the user ID; the application being configured to receive the plurality of device IDs from the device manager server, provide the device IDs to the SDK layer, such that the mobile device is paired with the plurality of remote devices, receive data from a remote device with a device ID that is one of the plurality of device IDs, and perform at least one of the following operations: store the data, display the data or send the data to a backend server, wherein the mobile device begins receiving measurements via the short range communication interface from at least one of the devices without needing to be paired or any further set up or action by a user.

These and other features, aspects, and embodiments are described below in the section entitled "Detailed Description."

BRIEF DESCRIPTION OF THE DRAWINGS

Features, aspects, and embodiments are described in conjunction with the attached drawings, in which.

DETAILED DESCRIPTION

Figure 1:
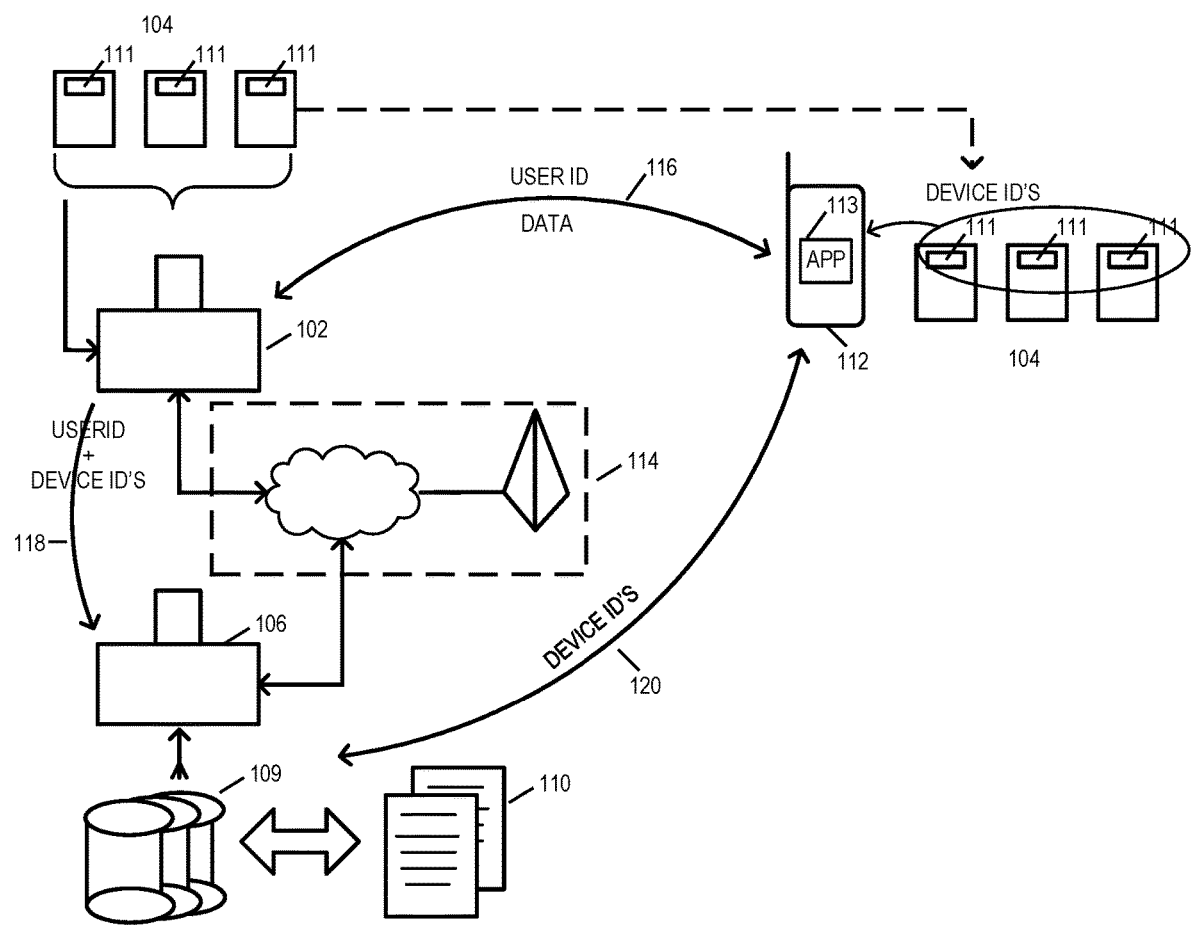
FIG. 1 is a diagram illustrating an example system for automatic pairing of devices in accordance with on embodiment.

FIG. 1 is a diagram illustrating a remote monitoring system 100 that allows automatic pairing of multiple devices. In system 100, a provider 102 provides multiple devices 104 to a user that is going to interface the devices with their mobile device 112 in order to collect and monitor multiple types of health or wellness information. It should be noted that devices 104 do not need to be health or wellness monitoring devices. The systems and methods described herein are equally applicable to other types of remote devices.

In system 100, the various entities or participants can communicate via a network 114 that can comprise various wired or wireless communication networks and capabilities. In the embodiment of FIG. 1, system 100 comprises the provider 102, which is the entity providing a service to or managing the user of mobile device 112. Device manager 106 will manage the relationship between the devices 104 and mobile device 112 as described below.

In system 100, a provider associated with provider system/server 102 is going to provide devices 104 to the user of mobile device 112. Devices 104 can come from device manager associated with device manager system/server 106 or a third party. The user will first download an application 113 associated with provider 102 and in setting up or registering the application 113, the application 113 will provide via a communication link 116 established through network 114, a user ID associated, with mobile device 112.

Provider 102 can then obtain the device ID for each of the devices 104 that are going to be sent to the user. The device ID(s) can comprise a MAC address for each device. For example, each device 104 can comprise a label 111 that includes a barcode or QR code that can be scanned or otherwise imaged in order to get the device ID or can be manually entered. The user ID and associated device ID are then sent to device manager 106 via a communication link 118 established via network 114, where it can be stored in database(s) 108, e.g., in table(s) 110.

Alternatively, the device IDs can be communicated wirelessly or via a wired connection from devices 104 to server 102.

Device manager 106 will then send the device IDs to mobile device 112 and application 113 via communication link 120 established via network 114. Application 113 now has the devices ID's for the devices it is going to interface with.

Once the user receives device 104, they can ensure that whatever interface mechanism, e.g., WiFi, Bluetooth, etc., being used is enabled, and then launch application 113. In other words, mobile device 112 and devices 104 will often have a short range communication interface that can be used to interface with other devices. As devices 104 connect with mobile device 112, application 113 will recognize the device IDs and automatically begin receiving and, depending on the embodiment, displaying data received from devices 104. The user does not have to do anything to pair devices 104 with mobile devices 112 and application 113, because the application 113 can provide the mobile device 104 with the device IDs so they are automatically paired, e.g., automatically recognized.

Of course, the user may have to set up the devices first and position them in order to make measurements and provide data. For example, the user may need to be sure the devices are plugged in or batteries installed and the devices turned on. In addition, the user typically has to interact with, wear, position, etc., the devices in order for them to gather data. For example, the user may have to put on a blood pressure cuff and activate it, or step on a scale, etc.

Once receiving information/data, application 113 can store the information on device 112 and/or send the information to provider 102 or some other back end for storage and analysis. This can allow for a much easier integration of data from multiple devices. Not to mention much greater adoption and adherence by improving the manner in which mobile devices, such as device 112 pair with remote monitoring devices 104.

In a more direct to consumer embodiment, the user of device 112 can simply purchase devices 104, e.g., off-the-shelf, and then use a scanner or camera included in device 112 to scan or image label 111 in order to obtain the device IDs. The device IDs can then be provided to application 113 to enable automatic information/data gathering as described above.

Figure 3:
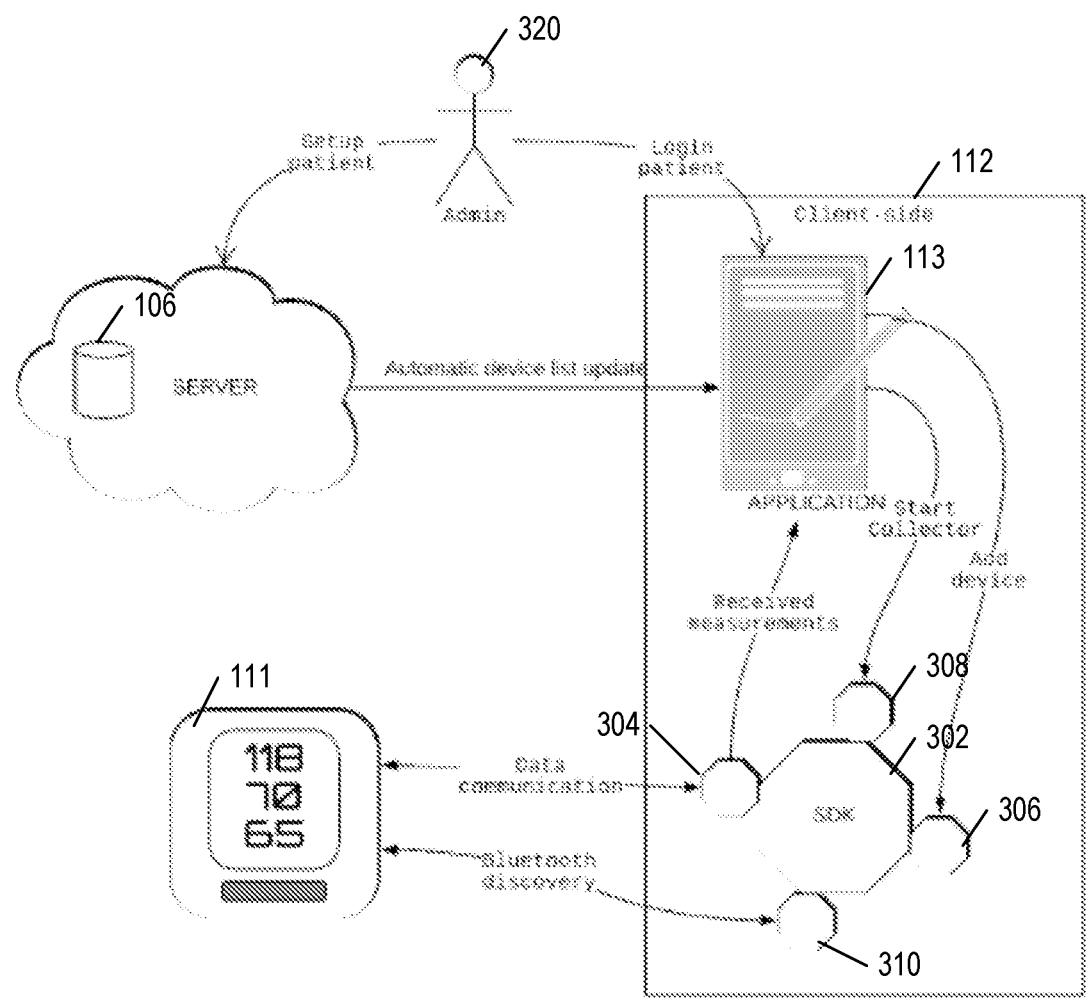
FIG. 3 is a diagram illustrating a mobile device used in the system of FIG. 1 according to an example embodiment.
Figure 4:
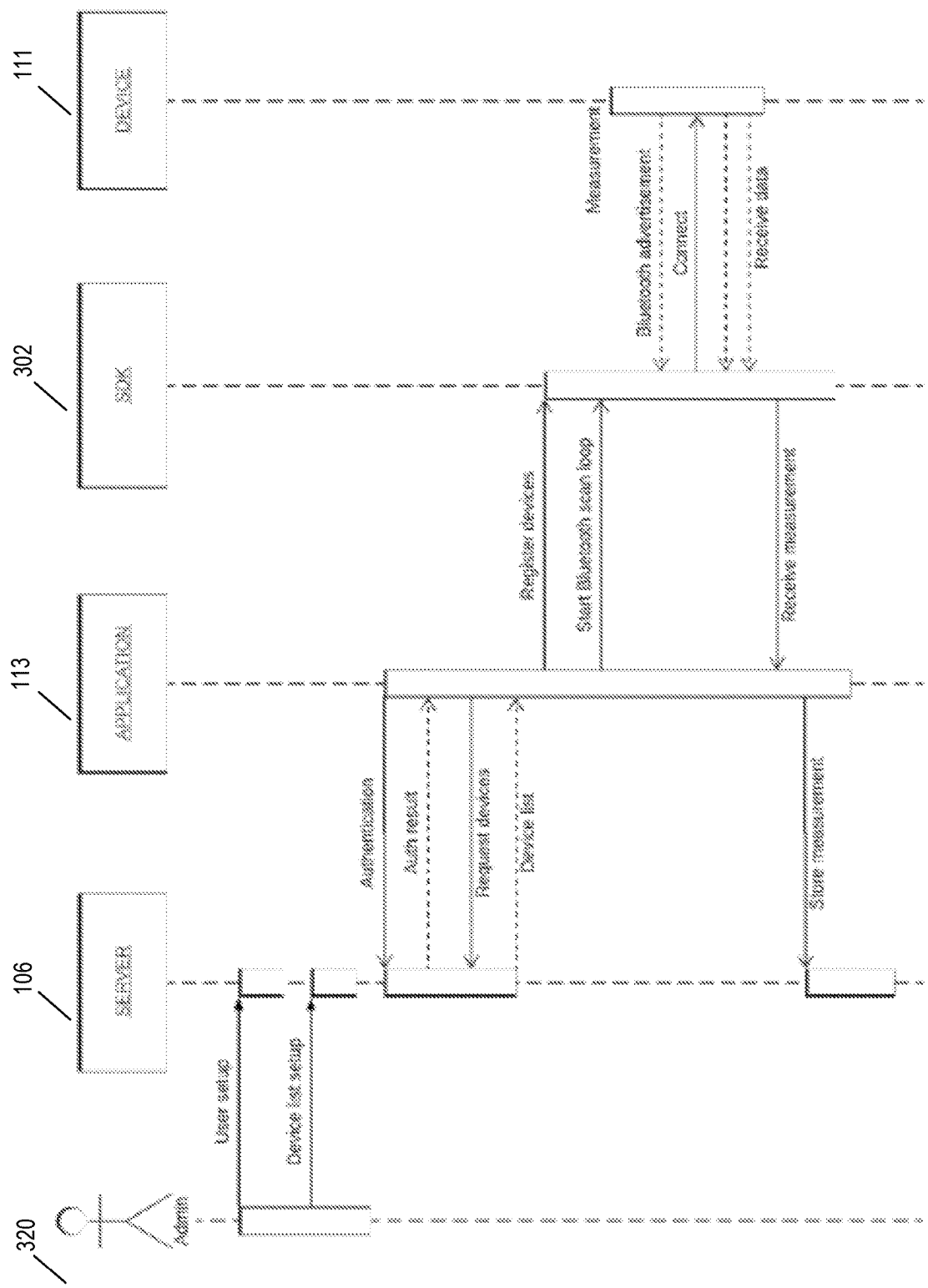
FIG. 4 is a diagram illustrating the sequence flow for the automatic pairing of devices in accordance with one example embodiment.

FIGS. 3 and 4 illustrated the automatic pairing described above. In FIG. 3, it can be seen that in addition to application 113, device 112 can include various software modules developed using an SDK 302 and associated with the interface mechanism, e.g., WiFi, Bluetooth, etc., include in device 112. The SDK 302 can be used to configure various modules/functionalities such as a data communication module 304 via the interface and between the device 111, in this case a blood pressure monitor, and application 113. As can be seen the server 106 can provide the device IDs that have been paired, by an administrator 320 with the user ID, which can then be provided to an add device module 306. Module 306 can then cause the device IDs to be stored at the Operating System (OS) and to be automatically paired with the device 112 with respect to the interface mechanism.

The application 113 can then activate data collection via a start collection module 308, which will then cause a discovery module 310 to determine whether any compatible devices are in range, in accordance with the protocol associated with the interface. When the discovery module 308 detects device 111, device 111 can immediately start providing data, without the need to pair with device 113, because it is already paired via the process described above.

FIG. 4 illustrates the sequence flow for the automatic pairing described in accordance with one embodiment. As can be seen, administrator 320 can associate the user and device IDs on server 106. Once application 113 is activated, it can connect with server 106 and authenticate itself to server 106. One authenticated, application 113 can then request the device list, i.e., list of device IDs. The device IDs can then be registered via the SDK layer 302, and scanning for the devices can begin. Once device 11 is connected, measurement data can then be provided to application 113 via the SDK layer 302. Application 113 can then store the data on server 106.

Figure 2:
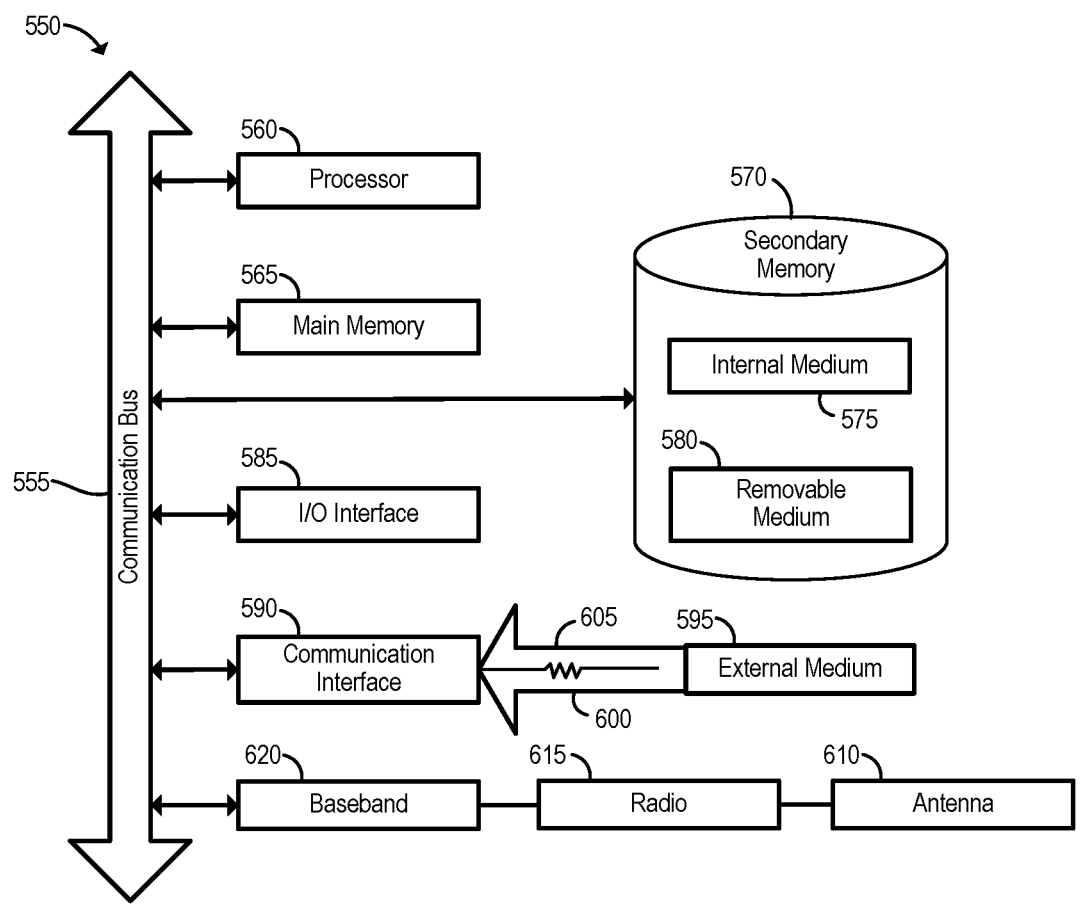
FIG. 2 is a diagram illustrating an example wired or wireless processing system that can be used in or to implement the system of FIG. 1 in accordance with another example embodiment.

FIG. 2 is a block diagram illustrating an example wired or wireless system 550 that may be used in connection with various embodiments described herein. For example the system 550 may be used as or in conjunction with the system 100, as previously described with respect to FIG. 1. The system 550 can be a conventional personal computer, computer server, personal digital assistant, smart phone, tablet computer, vehicle navigation and/or control system, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560, such as one or more of the modules described above. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that were previously described with respect to FIG. 3.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

While certain embodiments have been described above, it will be understood that the embodiments described are by way of example only. Accordingly, the systems and methods described herein should not be limited based on the described embodiments. Rather, the systems and methods described herein should only be limited in light of the claims that follow when taken in conjunction with the above description and accompanying drawings.

What is claimed:

1. A system comprising:
   a user device having a user identifier (ID), short range communication interface, an application, and a software development kit (SDK) layer;
   a remote system communicatively coupled to the user device and the application, and configured to
      obtain the user ID,
      obtain a plurality of device IDs associated with a plurality of remote devices,
      associate the user ID with the plurality of device IDs, and
      provide the plurality of device IDs to the application based on the user ID;
   wherein the application is configured to
      receive the plurality of device IDs from the remote system,
      provide the plurality of device IDs to the SDK layer in order to cause the user device to automatically pair with the plurality of remote devices based on receiving the plurality of device IDs,
      receive data from a remote device of the plurality of remote device via the short range communication interface of the user device, and
      perform at least one of the following operations: store the data, display the data or send the data to a backend server.

2. The system of claim 1, wherein the remote system is configured to provide the plurality of device IDs to the application after authenticating the application.

3. The system of claim 1, wherein the remote system comprises: a provider server communicatively coupled to the user device, a device manager server communicatively coupled to the provider server, and at least one database configured to store the associated user ID with the plurality of device IDs.

4. The system of claim 1, wherein the application is further configured to provide the data to the provider server.

5. The system of claim 1, wherein the application is further configured to receive a plurality of second device IDs associated with a plurality of second remote devices from the user device.

6. The system of claim 5, wherein the user device is configured to obtain the plurality of second device IDs via a scanner or a camera included in the user device.

7. The system of claim 1, wherein the remote system is configured to obtain at least some of the plurality of device IDs via a communication link separate from the user device.

8. The system of claim 1, wherein the plurality of device ID's are associated with one or more of: a scale, a blood pressure cuff, a glucose meter, and an activity tracker.

9. The system of claim 1, wherein each of the plurality of device IDs includes a MAC address.

10. The system of claim 1, wherein the application is further configured to perform one or more of: storing the data received from the remote device, sending the data to the remote system, and sending the data to a back end server.

11. The system of claim 1, wherein the user device further comprises a display, and wherein the application is configured to cause the data to be output to the display.

* * * * *